United States Patent
Muehlberg et al.

(12) 
(10) Patent No.: US 11,341,632 B2
(45) Date of Patent: May 24, 2022

(54) METHOD FOR OBTAINING AT LEAST ONE FEATURE OF INTEREST

(71) Applicant: Siemens Healthcare GmbH, Erlangen (DE)

(72) Inventors: Alexander Muehlberg, Nuremberg (DE); Rainer Kaergel, Forchheim (DE); Alexander Katzmann, Langensendelbach (DE); Michael Suehling, Erlangen (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 113 days.

(21) Appl. No.: 16/407,323

(22) Filed: May 9, 2019

(65) Prior Publication Data

US 2019/0355114 A1 Nov. 21, 2019

(30) Foreign Application Priority Data

May 16, 2018 (EP) ...................................... 18172664
Sep. 10, 2018 (EP) ...................................... 18193398

(51) Int. Cl.
*G06K 9/46* (2006.01)
*G06T 7/00* (2017.01)
(Continued)

(52) U.S. Cl.
CPC .............. *G06T 7/0012* (2013.01); *G06T 7/11* (2017.01); *G06T 7/174* (2017.01); *G06V 10/40* (2022.01);
(Continued)

(58) Field of Classification Search
CPC ......... G06T 7/0012; G06T 7/11; G06T 7/174; G06T 7/168; G06T 2207/10081;
(Continued)

(56) References Cited

U.S. PATENT DOCUMENTS 5,911,002 A * 6/1999 Mitsuyama .......... G01N 33/493
382/156
5,999,643 A * 12/1999 Shi ......................... G06N 3/063
382/158
(Continued)

FOREIGN PATENT DOCUMENTS

EP 3471054 A1 4/2019

OTHER PUBLICATIONS

Cheng, Ruida et al. "Automatic MR prostate segmentation by deep learning with holistically nested networks" Journal of Medical Imaging, vol. 4, No. 4, Oct. 2017 // DOI: 10.1117/1.JMI.4.4.041302.
(Continued)

*Primary Examiner* — Sean M Conner
*Assistant Examiner* — Stephen M Brinich
(74) *Attorney, Agent, or Firm* — Harness, Dickey & Pierce, P.L.C.

(57) ABSTRACT

A method is for obtaining at least one feature of interest, especially a biomarker, from an input image acquired by a medical imaging device. The at least one feature of interest is the output of a respective node of a machine learning network, in particular a deep learning network. The machine learning network processes at least part of the input image as input data. The used machine learning network is trained by machine learning using at least one constraint for the output of at least one inner node of the machine learning network during the machine learning.

22 Claims, 6 Drawing Sheets

(51) Int. Cl.
*G16H 30/40* (2018.01)
*G16H 50/20* (2018.01)
*G06T 7/11* (2017.01)
*G06T 7/174* (2017.01)
*G06V 10/40* (2022.01)

(52) U.S. Cl.
CPC ............. *G16H 30/40* (2018.01); *G16H 50/20* (2018.01); *G06T 2207/10081* (2013.01); *G06T 2207/20081* (2013.01); *G06T 2207/20084* (2013.01); *G06T 2207/30048* (2013.01); *G06T 2207/30096* (2013.01); *G06V 2201/031* (2022.01)

(58) Field of Classification Search
CPC . G06T 2207/10076; G06T 2207/20081; G06T 2207/20076; G06T 2207/20084; G16H 30/40; G16H 50/20; G16H 50/00

USPC .................................. 382/128–132, 155–158
See application file for complete search history.

(56) References Cited

U.S. PATENT DOCUMENTS

| | | |
|---|---|---|
| 2016/0019693 A1 | 1/2016 | Silbersweig et al. |
| 2016/0321522 A1* | 11/2016 | Yuan .................... G06N 3/0454 |
| 2018/0157899 A1* | 6/2018 | Xu ....................... G06K 9/4628 |
| 2019/0114767 A1 | 4/2019 | Muehlberg et al. |
| 2019/0191988 A1* | 6/2019 | Gargeya ................ A61B 5/725 |

OTHER PUBLICATIONS

European Search Report dated Apr. 8, 2019/.
Extended European Search Report dated Jul. 9, 2019.
European Communication dated May 6, 2021.

* cited by examiner

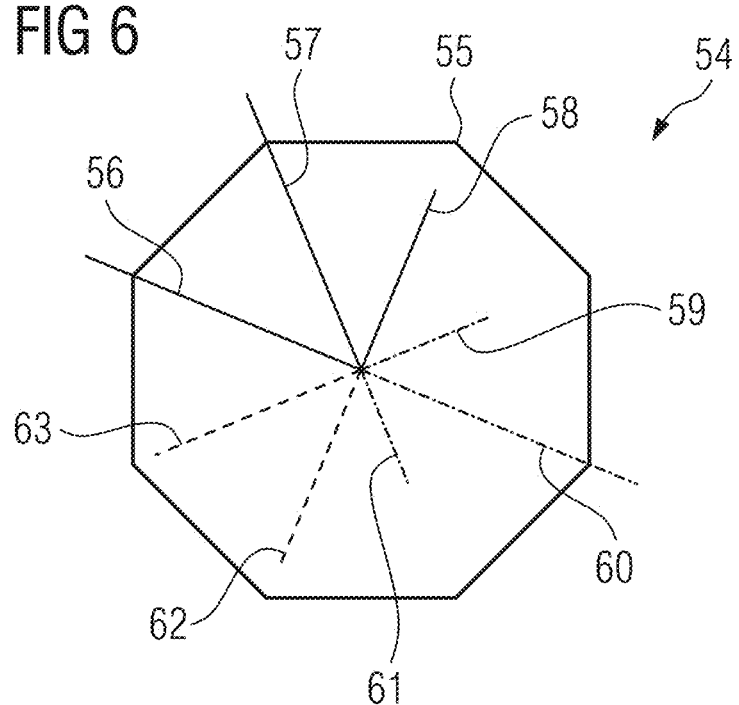
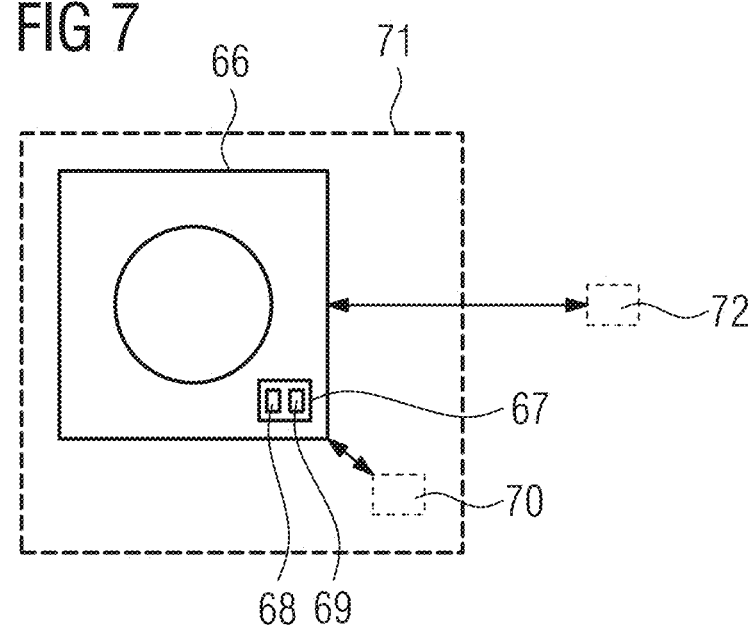

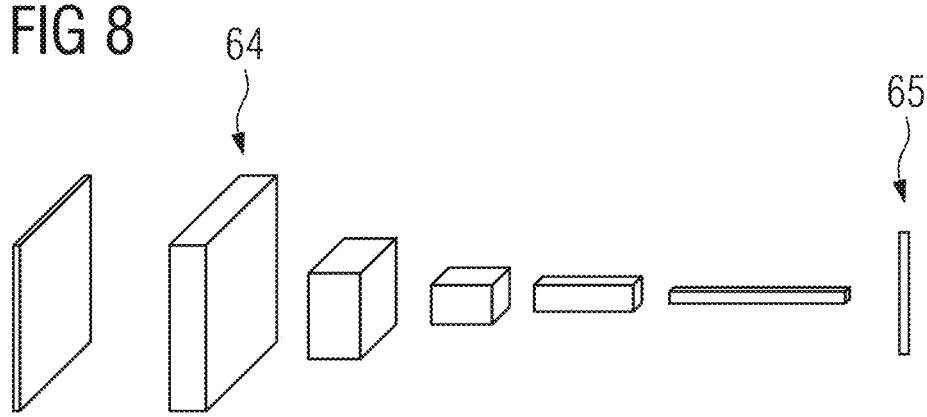

METHOD FOR OBTAINING AT LEAST ONE FEATURE OF INTEREST

PRIORITY STATEMENT

The present application hereby claims priority under 35 U.S.C. § 119 to European patent application numbers EP18172664.7 filed May 16, 2018, and EP18193398.7 filed Sep. 10, 2018, the entire contents of each which are hereby incorporated herein by reference.

FIELD

At least one embodiment of the application generally relates to a method for obtaining at least one feature of interest, especially a biomarker, from an input image, especially an input image acquired by a medical imaging device, wherein the feature of interest is the output of a respective node of a machine learning network, in particular a deep learning network, and wherein the machine learning network processes at least part of the input image as input data.

Embodiments of the application also generally relate to a processing system, a medical imaging device, a computer program and a computer-readable storage medium.

At least one embodiment of the application especially relates to a method and system for Feature-Enhanced Computed Tomography for Deep Learning yielding Quantitative Imaging Biomarkers. Specifically, at least one embodiment of the application relates to a method and system for obtaining data-driven biomarkers via machine learning, in particular deep learning.

Embodiments of the application are generally in the field of medical imaging and medical image analysis.

BACKGROUND

Medical imaging can be performed with a variety of imaging modalities such as X-ray, ultra sound, magnetic resonance imaging (MRI), computed tomography (CT), PET, SPECT etc. as are known in the art. The imaging is performed with a respective imaging device, also referred to as "scanner".

Quantitative Imaging Biomarkers Precision medicine strives to improve the clinical standard of care by enabling more accurate diagnosis and therapies that are tailor-made for the patient, thus maximizing the treatment response and reducing cost for all parties involved. A prerequisite for this is the existence of reproducible and standardized quantifications of the patient's properties of interest. It's necessary to standardize those measurements and adjust them for any covariates that might influence them in a systematic way. Only a measurement that is diagnostically relevant, precise and reproducible should be used as a biomarker.

In medical imaging there is a fundamental dichotomy between clinical studies and machine learning research. Clinical studies often use interpretable features that are currently hand-crafted. Those features are afterwards qualified in a post-hoc manner to ensure stability and interpretability of the selected features. The problem is that because the features are hand-crafted, the researcher must already know exactly what he is looking for and be able to express it in mathematical terms. Deep Learning systems, considered the state-of-the-art method for classification and regression tasks as in clinical decision support system, don't require manual feature engineering but instead derive image features automatically based on the input data. However, they suffer from a lack of interpretability and need a large amount of data. In addition to hindering the overall progress of research, the dichotomy of clinical studies and machine learning also creates a gap in communication and understanding between radiologists and machine learning specialists.

Machine learning networks, e.g. artificial neural networks typically consist of several layers of processing. The input image or sections of the input image and optionally additional data is fed to nodes, e.g. artificial neurons, of an input layer and the output of the nodes of the input layer gets fed to further layers of the network. The further layers comprise the output layer that provides the final result of the machine learning network, e.g. a classification of an object of interest in the input image, and optionally one or more hidden layers that provide data processing between the input layer and the output layer. Machine learning networks that comprise at least one hidden layer are considered to be deep learning networks.

The machine learning network can be trained by supervised learning. E.g. a training dataset can be provided that comprises pairs of input images and a desired output that should be generated by the machine learning network for the respective input image. The output can e.g. be a classification of an object of interest, e.g. a probable type of cancer or organ depicted in the input image, or it can be a probable value of a certain parameter, e.g. the risk of a major cardiac event.

We suggest to apply at least one constraint to the output of at least one inner node of the machine learning network during the machine learning. The inner node or inner nodes to which the constraint is applied can especially be nodes of a hidden layer of the machine learning network. It is however also possible to apply a constraint to the output of a node or multiple nodes of the input layer. Constraints to the outputs of the inner nodes can enforce a certain behavior of the node or nodes to which the constraint or constraints are applied. As discussed in more detail later these constraints can apply to additional input data that is provided with the input image or the constraints can enforce a dependence or independence of the outputs of several nodes.

The constraint can especially be a soft constraint. A violation of the constraint can therefore be penalized in a loss function that is minimized in the learning process. The loss induced for the violation of the constraint can scale with a degree of violation. A constraint for an inner node of the machine learning network can be considered to be a semantic constraint, since it is used to enforce a certain meaning or behavior of this inner node. The enforced behavior can e.g. be a correlation with a known additional information and/or with biomarker properties and/or an adherence to a certain model of an imaged object and/or the imaging process. Preferably, such a constraint is applied to the inner node that provides the feature of interest or at least one of the features of interest. This can be used to qualify and/or calibrate the feature of interest. The feature of interest can therefore be considered to be a qualified and/or calibrated feature.

Nodes of the machine learning network can e.g. be artificial neurons or clusters of artificial neurons. The output of inner neurons can be equivalent to the output of a certain filter or convolution kernel to the input image or a region of the input image or provide maximum or minimum detection for the input image, regions of the input image or the output of a previous filter.

The feature of interest can be a biomarker. Biomarkers are measurable indicators of biological states or conditions of an object of interest depicted in the input image. The method can therefore be considered to concern the generation of data-driven biomarkers.

The input image can be a two-dimensional image or a three-dimensional image, especially provided by medical imaging. The image can depict a patient or a part of a patient. It can especially be a computer tomography, but also be generated by different medical imaging protocols. The training of the machine learning network can especially be used to determine multiple free parameters of a machine learning network.

The feature of interest and/or the output of an output layer of the machine learning network can be an information that is usable to enable or support a user, especially a physician, in forming a diagnosis concerning a patient depicted in the input image. In other words, the feature of interest and/or the output of the output layer can be a diagnostically relevant feature. This can e.g. be achieved by using a constraint on an inner node that provides the feature of interest that enforces an output of this node that is approximately the same as a known biomarker. This can e.g. be achieved by using a training dataset that comprises a respective value of the respective biomarker for each input image wherein the difference of the value provided with a training dataset and the value generated by processing the respective input image is minimized. It is however also possible to generate a novel biomarker by using constraints to enforce a strong correlation between a certain output of the machine learning network and the output of the relevant inner node and/or by enforcing an independence of the output of that inner node from imaging parameters or non-relevant parameters of the imaged object.

The training dataset or some other dataset can then be used to determine a typical or average value for that certain biomarker e.g. in a certain cohort of a patient population. The diagnostically relevant features and/or features of interest that concern the image quality of the input image, e.g. a measure of the signal-to-noise-ratio, can then be displayed for a user to support or enable a diagnosis concerning the patient. Preferably, the values of the features of interest are displayed together with typical values of these features. E.g. a bar graph can be used. It was recognized that it can be especially advantageous to use a polygon, especially an octagon, wherein each corner or side is assigned to a particular feature of interest. Bars extending from the center of the polygon can extend exactly to the border of the polygon when the feature of interest has a typical or average value for a certain patient cohort. The respective bar can be longer or shorter when the value of the feature of interest exceeds this value or is below this value. The bars can be color coded for the type of feature displayed. E.g. different colors can be used for features of interest concerning the image quality, features of interest concerning predefined biomarkers, e.g. a spicularity or heterogeneity of a tumor, and for biomarkers newly discovered while training the machine learning network.

The machine learning network can process image data of a region of interest and at least one control region of the input image, wherein the feature of interest and/or the output of the or an output layer of the machine learning network describes a property of an object of interest that is expected to be independent of the image data in the control region, wherein the feature of interest and/or the output of the output layer depends on the image data of the region of interest and the control region. This approach can be advantageous since the actual image data in the region of interest depends on the property of the object of interest and on further parameters, especially imaging parameters, e.g. a noise level, and/or parameters of the depicted patient, e.g. a weight or a body-mass index of the patient. In many cases the influence of these further parameters on the feature of interest and/or the output of the output layer can be reduced by considering image data that was acquired in the control region. The control region can e.g. be an air-filled region or a region that only comprises adipose tissue. Preferably the control region is chosen to be essentially homogeneous and to be not or hardly influenced by the property of the object of interest. The machine learning network can then be trained in such a way that the influence of the further parameters on the feature of interest or the output of the output layer can be reduced dependent on the image data of the control region, especially dependent on features extracted from the control region.

The output of at least one of the inner nodes can be independent of the image data of the control region or regions and especially only depend on the image data in the region of interest. A collection of features determined from the region of interest can be labeled RADIOME. These features depend on the object of interest and on the further parameters. To remove or reduce the influence of the further parameters the output of at least one further inner node can be used, which is independent of the image data in the region of interest and especially only depends on the image data in one or more control regions. Features extracted by this type of inner node can be called TECHNOME, since they primarily depend on parameters of the image acquisition and/or further properties of the depicted object that influence the image quality.

In the European patent application EP 17 196 657 which was not yet published, the entire contents of which are hereby incorporated herein by reference, the idea of using TECHNOME features extracted from a control region to correct RADIOME features extracted from a region of interest was already discussed. It was found that algorithms used to extract the TECHNOME features should satisfy a number of conditions to allow for an optimum correction of the RADIOME features. The approach discussed in this previous application uses a large number of candidate algorithms and then applies certain tests to them to select good algorithms. In the context of a machine learning network, the TECHNOME can be provided by the output of certain inner nodes that do not process input data from the region of interest. The RADIOME can be associated with the output of certain inner nodes that do not process any input data from the control regions. The conditions that can be applied to select the algorithms used to determine the TECHNOME in the prior application can already be considered during the learning process. This can be achieved by using constraints for the inner nodes that enforce these conditions. Possibilities for implementing certain useful conditions will be discussed in more detail later on.

Dependencies between the output of a node and an additional information provided with a respective input image or the output of another node can often not be recognized when processing individual images. While a simple constraint like an approximate identity between the output of the node and an additional information provided with the input image can be enforced by using a loss function that sums a measure of the deviation for each image, more complex relations like e.g. a covariance or other statistical dependencies between outputs for different nodes or the output of a node and an additional information provided with input image can only be checked when collectively processing multiple images.

It is therefore possible that a training dataset used to train the machine learning network is split into multiple subsets, wherein the machine learning network is trained by combining multiple identical copies of the machine learning network or of at least one given subsection of that network into a merged network, wherein each of the copies processes input data from one of the input images of the respective subset, wherein the copies are coupled by at least one additional processing node or processing layer of the merged network that provides a respective input for at least two copies of the machine learning network or subsection for the output of the respective inner node or of at least one of the respective inner nodes to which the constraint should be applied and outputs a measure of the fulfilment of that constraint that depends on the outputs of the respective inner nodes of the copies. With this approach it can e.g. be recognized if there is a dependence, especially a linear dependence, between the outputs of multiple inner nodes and/or between the output of an inner node and an additional information provided with the respective input image. With sufficiently sized subsets any type of statistical correlation or dependence between the outputs of two nodes or between the output of a node and an additional information provided with input image can be checked. It can therefore also be determined if outputs of two nodes are essentially orthogonal or if the output of a node is essentially orthogonal to a provided additional information.

It is already known that subsets of a training dataset, so-called minibatches, can be used to train machine learning networks. E.g. a loss can be calculated for all images in a minibatch and only after the complete minibatch has been processed, the loss can be back propagated through the machine learning network. The described method extends this idea by using constraints that evaluate the output of a certain node for multiple input images. The measure of the fulfilment of the constraint can be used as loss function or can be the loss function and can therefore be minimized or maximized by training the machine learning network.

At least one of the subsets can comprise input images generated by a simulation of the image generation, especially of a measurement and/or reconstruction process used to provide the input image, or by a modification of a provided input image, wherein a parameter of the simulation of the image generation or the modification is varied across the subset, wherein the constraint or at least one of the constraints concerns a dependence or independence between the output of at least one inner node of the machine learning network and the varied parameter. This approach can especially be used to train the network to provide an output of one or more inner nodes that is dependent on a specific parameter of the imaging process or the reconstruction process. E.g. the image can be modified by adding increasing amounts of noise to ensure a dependence, especially a correlation, of the output or the outputs of the inner node or inner nodes to the noise level. On the other hand, this approach can be used to explicitly decouple or decorrelate the output of an inner node or inner nodes from the varied parameter. This can e.g. ensures that the feature of interest is independent of previously known features, e.g. a body mass index or the weight of the patient and/or is independent of imaging parameters.

As previously discussed, at least one of the inner nodes can output a value generated from a control region of the input image that describes an imaging parameter, e.g. a noise level. This parameter or a set of parameters, also called TECHNOME, can be used to correct a RADIOME, namely outputs of inner nodes that concern features of an object of interest that are generated from a region of interest. To allow for this correction the output of a node or subnet generating a feature of the TECHNOME should be associated with the output of the same subnet or node when applied to the region of interest, since only in this case the TECHNOME will be useful for correcting the RADIOME. The machine learning network or a merged network used during the training of the machine learning network can therefore comprise a copy of the subnet used to generate the TECHNOME that uses image data from the region of interest as input data instead of input data from the control region. The constraint can then enforce a dependence and therefore an association, especially a correlation, between the outputs of these copies of the subnet.

The constraint or at least one of the constraints can concern a dependence or independence of at least one first inner node of the machine learning network on or off the output of at least one second inner node of the machine learning network for the input images or the or a subset of the input images of the or a training dataset used for training the machine learning network. For example, the previously discussed copy of the subnet or node used to generate the TECHNOME that is applied to the region of interest can provide an output of the first inner node and a subnet or node trained to extract a feature of interest concerning the object of interest can provide the output of the second inner node. By applying a constraint that enforces an independence or orthogonality between these outputs during the training, e.g. by adding a term to the loss function that depends on a measure of correlation between these outputs, the subnet or node providing the RADIOME can be trained to provide an image filter that is developing orthogonally to the TECHNOME image filter. Therefore, the TECHNOME features can correct the RADIOME features for the impact of technical variations while the RADIOME is simultaneously predicting the diagnostically relevant clinical response.

A constrain enforcing the dependence of the output of the subnet or node used to extract the TECHNOME from the control region or regions to the output of the same subnet or node when applied to the region of interest can also be enforced by maximizing a measure of similarity between the outputs of the respective inner nodes.

A constraint enforcing the independence of outputs of the first and second inner node can also be used to ensure that the subnet or node providing the RADIOME as the output data is orthogonal to a benchmark model that is used to safeguard against poor study design. The benchmark model can be created by trying to train the machine learning network using only data outside the region of interest. Since these regions cannot contain most of the biologically relevant information the benchmark model should only be able to predict a response variable if the response is confounded with acquisition or reconstruction parameters.

Constraints concerning the dependence or independence of the outputs of nodes or the output of a node with additional information provided with each input image can be intended to minimize or maximize a measure of dependence, especially a statistical measure of dependence, e.g. the correlation between the values. Additionally, or alternatively to the correlation other information-theoretic measures can be used. The measurement of the dependence can also comprise more complex tests, e.g. a measure of how well the dependence fits a linear dependence. This can be advantageous since in the case where a TECHNOME is used to correct a RADIOME it is advantageous to use a linear correction.

Concerning the previously discussed first inner node and second inner node it is possible that the first inner node depends exclusively on data taken from a respective first region of the respective input image and that the second inner node depends exclusively on data taken from a respective second region of the respective input image. The first region can be the region of interest and the second region can be a control region. This type of constraint for the output of the inner nodes can e.g. be used to ensure that an algorithm implemented by a subnet comprising the respective inner node has a similar or an orthogonal behavior when applied to the region of interest and to the control region. It is also possible that the first region and the second region are separate control regions. Such a constraint can be used to e.g. ensure a similar behavior of algorithms implemented by certain subnets when copies of the subnet are applied to different control regions.

The machine learning network can be designed in such a way that the first and second inner node generate the same output when the first and second inner node or a first subnet of the machine learning network comprising the first inner node and the second subnet of the machine learning network comprising the second inner node are processing the same input data. A preferred embodiment of this can be realized by using identical copies of a node as the first and second inner node or by using identical copies of a subnet of the machine learning network as a first and a second subnet. By using this approach the identical algorithm implemented by the respective subnet or inner node can be applied to image data from different regions to compare the behavior of the respective algorithm in these regions.

The first subnet can comprise all nodes on whose output the first inner node depends and the second subnet can comprise all nodes on whose output the second inner node depends.

In an alternate embodiment or for another constraint used in the training of the machine learning network the first inner node and the second inner node can depend on the same data taken from the respective input image. In this case it is advantageous if the first node and/or the subnet of nodes providing input data for the first inner node and the second inner node or a subnet providing input data to the second inner node implement a different algorithm for processing the input data. This can be achieved by using different network architectures. In a preferred embodiment this is however achieved by using an independent parametrization of the inner nodes and/or the subnets feeding those inner nodes.

The machine learning network can e.g. be trained in such a way that the first inner node or a first subnet comprising the first inner node is a copy of an original node or subnet, wherein the original node or subnet extracts a feature concerning an object of interest from the image data of the region of interest, and wherein the copy processes image data from a control region. The first inner node or the subnet comprising the first inner node can therefore implement a copy of an algorithm that is used to extract the RADIOME or a part of the RADIOME from the region of interest and the output can be the result of applying this algorithm to image data from a control region. The second inner node or a subnet comprising the second inner node can be used to extract the TECHNOME and therefore features of interest not concerning the object of interest, especially imaging parameters or general parameters of a patient not related to the object of interest, e.g. a body mass index, from the control region. By applying a constraint that increases a loss when a dependence, especially a statistical dependence, between these outputs is detected, the algorithms that generate the TECHNOME and the RADIOME can be trained to be essentially orthogonal, so that the RADIOME can be corrected by the TECHNOME without changing relevant features recovered for the object of interest.

The or a training dataset used for training the machine learning network can comprise additional information for each input image of the training dataset, wherein the fulfilment of the constraint or at least one of the constraints for the inner node or at least one of the inner nodes concerns a dependence or independence between the output of the respective inner node and the additional information for the input images or a subset of the input images in the training dataset. The additional information can especially be non-image information. The additional information can e.g. concern imaging conditions like a noise level or known parameters of a medical imaging device used to acquire the image or of the imaging protocol used.

The additional parameters can additionally or alternatively concern features of a patient influencing the image but not directly relevant to the object of interest, e.g. a body mass index, an age or previously known features depicted in the image data. The additional information can also concern a prior segmentation of the respective input image, diagnostic information and/or anatomic labels for certain features or segments. A condition concerning anatomic labels provides additional information and can especially ensure that the TECHNOME extracted from an input image is essentially independent of these labels. This allows for using TECH-NOME features extracted from a control region to be used for a correction of RADIOME features in the region of interest, since the part of the machine learning network determining the TECHNOME is trained in such a way that the features are independent of anatomic labels and therefore of the anatomic region in which the respective feature is determined.

A special case of the use of additional information is a training of the machine learning network in such a way that certain conditions for certain inner nodes are only active for input images or sub batches comprising only input images that provide certain additional information. This can e.g. be used to only evaluate certain conditions for certain types of input images, e.g. input images generated by simulation or input images generated via phantom measurements.

The or a training dataset or at least one of the training datasets used for training the machine learning network can comprises input images that where generated by imaging a phantom or by simulation of an imaging of a digital phantom, wherein a technical imaging parameter used in the generation or reconstruction of the respective input image is varied between the input images, wherein the technical imaging parameter or a measure that is dependent on the technical imaging parameter is provided as additional information for the respective input image, wherein the constraint or at least one of the constraints is a constraint for an inner node whose output depends on image data from the or a region of interest of the respective input image and concerns a dependence between the output of that inner node and the technical imaging parameter or the measure that is dependent on the technical imaging parameter.

When using input images generated by simulation or by scanning a phantom the additional information can describe a variation in a certain technical parameter and a constraint can concern a strong response, e.g. a strong correlation, of the output of the inner node to that parameter. As previously discussed the machine learning network can be trained in such a way that a subnet or node of the network extracts a TECHNOME from a control region. During the training a copy of this node or the nodes forming this network can be used to process the region of interest of the input image or input images generated by simulation or phantom scans. If the output of at least one node of this copy is trained to be strongly correlated or show another strong response to a variation of the technical parameter, this ensures that an application of the algorithm trained in that way to the control region will yield data that is relevant to correct the RADIOME features extracted from the region of interest, since it was shown in simulations or phantom studies that changes of that technical parameter strongly influence the output of the algorithm for the region of interest.

Preferably the machine learning network is trained using at least one additional constraint for the output of at least one output node of an output layer of the machine learning network, especially an output node whose output depends on the feature of interest and/or the output of the inner node to which the constraint or at least one of the constraints is applied during training.

The output layer of the machine learning network can e.g. classify an object of interest in the region of interest or provide a regression for a feature of the object of interest. The output of the output layer can especially be an information of known medical relevance. It can e.g. be a probability of a major cardiac event when the heart of a patient is imaged in the input images or it can be a classification if a depicted object is more likely to be a malign or benign tumor.

In the simplest case the constraint can ensure that the output of the trained machine learning network is similar to additional information provided with each input image of the training dataset. If the previously discussed constraints for inner nodes are not used during the training of the machine learning network this is equivalent to a normal supervised learning. As already discussed in the introduction a normal supervised learning can already provide highly relevant information. The additional constraint is however especially advantageous when combined with the previously discussed constraint for at least one inner node. If only constraints concerning inner nodes, also called semantic constraints, are used, the machine learning network can be trained to output at least one feature of interest on the output of an inner node that is decoupled from at least some technical influences or influences of patient parameters not related to an object of interest. While this kind of training can be relevant for some application, typically it is desirable to only generate features that are relevant for a certain diagnostic task that can be solved by a medical professional based at least in part on the features generated by the trained machine learning network. The relevance for a specific medical information, especially for a diagnostic task, can be ensured by using the additional constraint for the output of the output layer.

SUMMARY

At least one embodiment of the invention provides improved image processing by a machine learning network, wherein the interpretability of the results is improved and/or wherein a training of the machine learning network can be achieved with a reduced amount of data.

At least one embodiment of the invention provides improved image processing, wherein the used machine learning network is trained by machine learning using at least one constraint for the output of at least one inner node of the machine learning network during the machine learning.

In an embodiment of the invention, the constraint or constraints to the inner nodes and the constraint to the at least one output node of the output layer are applied during the complete training of the machine learning network. It is however also possible to alternate the application of the constraints. The machine learning network can e.g. at first be trained only using the additional constraint for the output of the output node and after a first iteration of the training the training can be switched to a constraint or to constraints for at least one inner node or vice versa. This alternating use of constraints can be repeated for a given number of times or until a convergence condition is fulfilled.

In an embodiment of the invention, a processing system comprises:
  at least one processor, configured to obtain at least one feature of interest from an input image acquired by a medical imaging device, the at least one processor being configured to:
    process, via a machine learning network, at least part of the input image as input data;
    train the machine learning network by machine learning using at least one constraint for an output of at least one inner node of the machine learning network during the machine learning; and
    obtain the at least one feature of interest from an output of a node of a machine learning network.

In an embodiment of the invention, a method is disclosed for obtaining at least one feature of interest from an input image acquired by a medical imaging device, the method comprising:
  processing, via a machine learning network, at least part of the input image as input data;
  training the machine learning network by machine learning using at least one constraint for an output of at least one inner node of the machine learning network during the machine learning; and
  obtaining the at least one feature of interest from an output of a node of the machine learning network.

Besides the inventive method, embodiments of the application also concern a processing system configured to perform the method according to an embodiment of the present invention. The processing system can comprise a processor and a memory unit. The memory unit can store a program that implements the discussed method and the processor can execute the programming instructions to perform the method.

At least one embodiment of the invention also concerns a medical imaging device, especially a computer tomography device, concerning the processing system according to an embodiment of the present invention. An integration of the processing system into a medical imaging device can be advantageous since certain imaging parameters that are typically not stored with medical imaging data can be processed as additional non-image information by the machine learning network. This additional data can be used only during the training of the machine learning network. Preferably, it is however also used as additional input data when determining the feature of interest by the trained machine learning network.

In an alternate embodiment, the processing system could be a separate device from the medical imaging device. It could e.g. be a device located in the same building, especially in the same room or an adjacent control room to the medical imaging device, and can e.g. serve to provide data to a user of the medical imaging device. The processing system could also be a server that could be in the same building or that could be distant from the building or it could be implemented as a cloud solution comprising several servers that are not necessarily located in the same location.

At least one embodiment of the invention also concerns a computer program that can be directly loaded into a memory unit of a processing unit, especially a processing unit of a medical imaging device, the computer program comprising instructions for performing the steps of at least one embodiment of the inventive method when the program is executed on the processing unit. Additionally, at least one embodiment of the invention concerns a computer-readable storage medium containing electronically readable instructions comprising the computer program according to at least one embodiment of the invention.

At least one embodiment of the invention also concerns a method for training a machine learning network. The machine learning network can be trained as discussed with respect to the method for obtaining at least one of the features of interest.

At least one embodiment of the invention also concerns a machine learning network trained by this method and a computer-readable storage medium containing information representing this trained machine learning network.

Embodiments of the present invention relate to methods as generally described herein, in particular for obtaining data-driven biomarkers via machine learning.

At least one embodiment of the present invention further relates to a method for obtaining data-driven biomarkers via machine learning using additional and/or prior information in every layer of a machine learning network, in particular a deep learning network.

At least one embodiment of the present invention further relates to a system for obtaining data-driven biomarkers via machine learning comprising a machine learning network, in particular a deep learning network.

At least one embodiment of the present invention further relates to a computer program, which performs the steps of at least one embodiment of the methods according to the invention if the computer program is executed on a computer.

At least one embodiment of the present invention further relates to an electronically readable storage medium, on which the computer program is stored.

BRIEF DESCRIPTION OF THE DRAWINGS

Specific embodiments of the invention will be described in detail herein below with reference to the figures wherein the figures show schematically.

DETAILED DESCRIPTION OF THE EXAMPLE EMBODIMENTS

Figure 1:
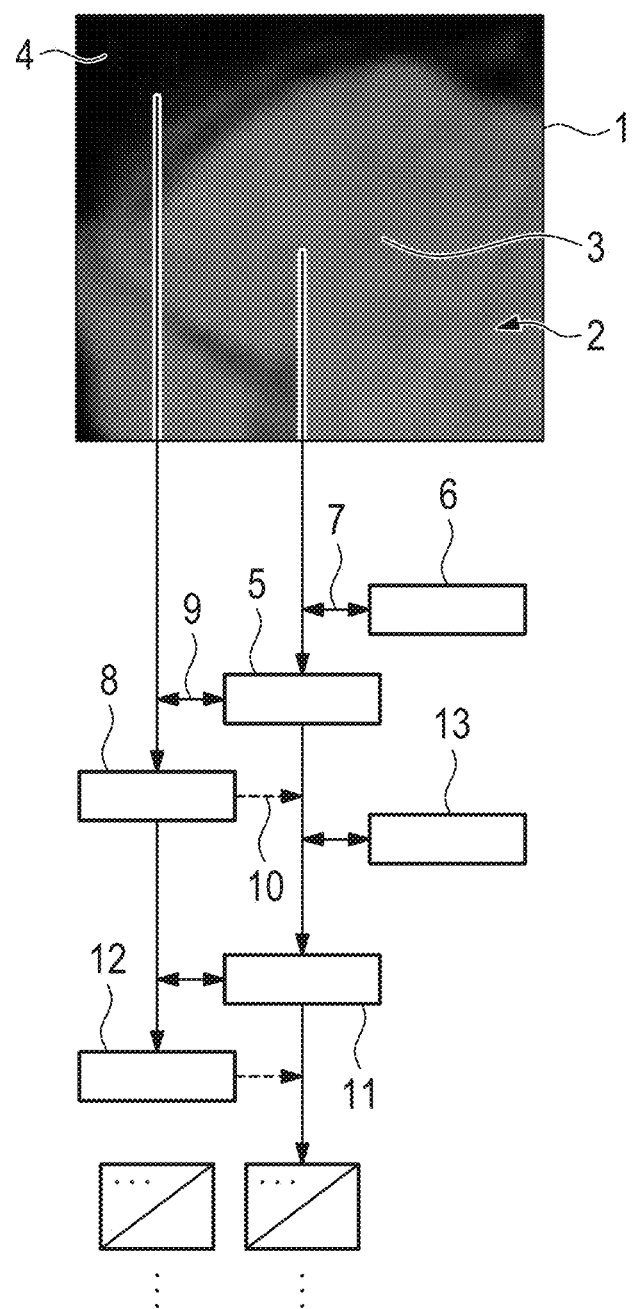
FIG. 1 The extraction of features of interest from an input image and the decorrelation of a TECHNOME concerning technical features of the image acquisition and a RADIOME concerning features of an object of interest that can be achieved by constraints on inner nodes of the machine learning network during the learning process in an embodiment of the present invention, FIG. 2 a Deep Learning architecture with integrated semantic constraints for outputs of inner nodes of the machine learning network used in an embodiment of the present invention, FIG. 3 an example of the detailed structure of a subnet of the machine learning network shown in FIG. 2, FIG. 4 a flow chart of an embodiment of a method for obtaining at least one feature of interest from an input image according to the present invention, FIG. 5 the output of an inner node during a training of the machine learning network, FIG. 6 a possible visualization for features of interest extracted from an input image in an embodiment of the present invention, FIG. 7 an embodiment of a medical imaging device according to the present invention comprising a processing system according to an embodiment of the present invention, also showing possible other embodiments of a processing system according to the present invention, and FIG. 8 a visualization of the output of the machine learning network and the corresponding Deep Learning network layers.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing"

or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without subdividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

In an embodiment of the invention, the constraint or constraints to the inner nodes and the constraint to the at least one output node of the output layer are applied during the complete training of the machine learning network. It is however also possible to alternate the application of the constraints. The machine learning network can e.g. at first be trained only using the additional constraint for the output of the output node and after a first iteration of the training the training can be switched to a constraint or to constraints for at least one inner node or vice versa. This alternating use of constraints can be repeated for a given number of times or until a convergence condition is fulfilled.

Besides the inventive method, embodiments of the application also concern a processing system configured to perform the method according to an embodiment of the present invention. The processing system can comprise a processor and a memory unit. The memory unit can store a program that implements the discussed method and the processor can execute the programming instructions to perform the method.

At least one embodiment of the invention also concerns a medical imaging device, especially a computer tomography device, concerning the processing system according to an embodiment of the present invention. An integration of the processing system into a medical imaging device can be advantageous since certain imaging parameters that are typically not stored with medical imaging data can be processed as additional non-image information by the machine learning network. This additional data can be used only during the training of the machine learning network. Preferably, it is however also used as additional input data when determining the feature of interest by the trained machine learning network.

In an alternate embodiment, the processing system could be a separate device from the medical imaging device. It could e.g. be a device located in the same building, especially in the same room or an adjacent control room to the medical imaging device, and can e.g. serve to provide data to a user of the medical imaging device. The processing system could also be a server that could be in the same building or that could be distant from the building or it could be implemented as a cloud solution comprising several servers that are not necessarily located in the same location.

At least one embodiment of the invention also concerns a computer program that can be directly loaded into a memory unit of a processing unit, especially a processing unit of a medical imaging device, the computer program comprising instructions for performing the steps of at least one embodiment of the inventive method when the program is executed on the processing unit. Additionally, at least one embodiment of the invention concerns a computer-readable storage medium containing electronically readable instructions comprising the computer program according to at least one embodiment of the invention.

At least one embodiment of the invention also concerns a computer-readable storage medium containing at least one feature of interest generated or generatable by at least one embodiment of the inventive method. The feature of interest can be the output of at least one inner node of the machine learning network, especially of at least one inner node to which a constraint was applied during the machine learning. The feature or features of interest can be stored for various purposes. The feature of interest can be stored directly in a DICOM file as additional DICOM frame or frames or as DICOM metadata. This can already happen in the medical imaging device or the DICOM file can be annotated at a later point, e.g. by a cloud service. Adding at least one feature of interest to a DICOM file or other patient data can be advantageous, when the feature of interest is intended to assist a medical professional in forming a diagnosis. These options for storing the feature or features of interest will be discussed in more detail later.

It is also possible to store features of interest in separate files for later use, e.g. for training other machine learning networks or for providing statistical data for a certain patient cohort. Various formats for storing features of interest on a computer-readable storage medium namely as a RADIOME filter image array, a RADIOME feature array or as specialized RADIOME features, will be discussed in more detail later.

At least one embodiment of the inventive method can especially be used to decouple or decorrelate specific features of an object of interest depicted in a region of interest in the input image from technical imaging parameters and/or parameters of a patient that do not concern the object of interest and/or that are already know or should be determined by other device(s). By using constraints on inner nodes the machine learning network can therefore e.g. be trained to output a filtered image or a filtered section of the input image or filtered features as features of interest, wherein the influence of the imaging parameters or the discussed parameters of the patient on this output is removed or reduced. The filtered image or section or features can then be directly used for further processing, e.g. by a further algorithm, especially a further machine learning network, or be used to train other machine learning solutions. This allows the method to act as a universal preprocessing for a multitude of purposes. It can however be advantageous to first store the filtered image or section or parameters on a computer-readable storage medium to e.g. provide the data to other users at a later point in time.

The computer-readable storage medium can also contain the input image from which the feature of interest is generated. In this case the method according to at least one embodiment of the present invention can be used to check if at least one embodiment of the inventive feature was generated by using such a method.

At least one embodiment of the invention also concerns a method for training a machine learning network. The machine learning network can be trained as discussed with respect to the method for obtaining at least one of the features of interest.

At least one embodiment of the invention also concerns a machine learning network trained by this method and a computer-readable storage medium containing information representing this trained machine learning network.

We propose a unified system for imaging biomarker qualification integrated with Deep Learning-based predictions that overcomes the issues mentioned in the introduction.

As stated above, the biomarker qualification on one hand in clinical studies and Deep Learning-based predictions on the other are currently two separate disciplines. An important technique which deals with semantic constraints in a post-hoc manner without employing Deep Learning is Similar Additive Linear Surrogate Association, in short SALSA, which is disclosed in the currently unpublished application EP 17 196 657, internal ID 2017E17274DE, which uses inter-patient associations of image information, imaging-system-specific simulations, scan parameter variation analysis on phantom data and further post-hoc constraints to identify the image content that can be used to calibrate the respective features against image quality variation. All features measured in a region of interest (ROI) are called RADIOME and all features quantifying technical variation (surrogates) in other parts of the image, which we call control regions (CR), are called TECHNOME.

The TECHNOME consists of surrogates which are—similar to biomarker feature qualification—qualified to calibrate the RADIOME. This qualification process can be described by semantic constraints, such as a linear relationship between RADIOME and TECHNOME or that the association between the components of RADIOME and the TECHNOME shall be reproducible via simulations. The RADIOME and the TECHNOME however consist of hand-crafted features. The proposed system enables the simultaneous construction of RADIOME and TECHNOME by way of Deep Learning that is steered not only by the diagnostic relevant question but also by those semantic constraints. The proposed system can thus be used as a Deep Learning-based joint data-driven construction of TECHNOME and RADIOME. Solving other tasks like constructing a RADIOME that is invariant to the influence of the body-mass-index (BMI) is possible too.

The learning process of Deep Neural Networks (DNN) is currently steered by two things: The target output variable that shall be discriminated (e.g. a variable relevant diagnosis for "type of tumor: more likely benign vs. malign") and the network architecture chosen by the technical designer of the network. In current designs no semantic constraints on any part of the network between the input image and the output variable are enforced, thus rendering it a "black box" for the most part. Getting insight into the semantics of Deep Learning-induced features is currently limited to simple things like visualizing the learned convolutional filters (in the case of Convolutional Neural Networks) or visualizing regions of the input image after being filtered. Both options are far too low-level and technical to help making the semantics of a Deep Neural Net interpretable to those unfamiliar with the inner technical workings of artificial neural networks, e.g. radiologists. Even to the designer of the network, getting semantic insight beyond the convolutions remains elusive.

Embodiments of the present invention relate to methods as generally described herein, in particular for obtaining data-driven biomarkers via machine learning.

At least one embodiment of the present invention further relates to a method for obtaining data-driven biomarkers via machine learning using additional and/or prior information in every layer of a machine learning network, in particular a deep learning network.

At least one embodiment of the present invention further relates to a system for obtaining data-driven biomarkers via machine learning comprising a machine learning network, in particular a deep learning network.

At least one embodiment of the present invention further relates to a computer program, which performs the steps of at least one embodiment of the methods according the invention if the computer program is executed on a computer.

At least one embodiment of the present invention further relates to an electronically readable storage medium, on which the computer program is stored.

In order to bridge the gap between clinical studies and Deep Learning, a novel method for obtaining data-driven biomarkers via machine learning is presented here. The usual post-hoc biomarker qualification is transformed to a-priori semantic constraints on the features that are automatically derived by a Deep Learning network, lending interpretability to the system. Compared to existing Deep Learning systems that incorporate non-image information as additional inputs to the classification layers and thus after the image feature layers, the new system uses additional and prior information in every layer of the network and thus infers features that are explicitly orthogonal to epidemiological data like BMI and age or existing image features. This makes it possible to automatically create features containing information that is not already available without a CT scan while requiring fewer available annotated data points than comparable systems.

Similar to existing Deep Learning procedures, the proposed system uses artificial neural networks with a specific data cohort as its input, e.g. CT scans of patients in the case of medical imaging. However, common existing approaches only optimize one overall loss function in their last layer to minimize the average difference between predefined labels (e.g. "benign or malign tumor") and the network's output (see e.g. FIG. 2). This can be viewed as a "discriminative loss", because it quantifies how well the created model can discriminate input data into different groups (categorical for classification or continuous for regression).

The first principal idea of the proposed system is to introduce additional "semantic losses" which enforce semantic constraints that are meaningful for the task to solve. They can be modeled analogously to post-hoc semantic constraints like SALSA so that the features derived by the proposed system undergo the same rigorous calibration and qualification process that enables them as biomarkers. However, as the proposed system enforces the semantic constraints as part of the optimization process of the Deep Learning network instead of post-hoc, the system automatically learns novel biomarkers that are qualified by the semantic constraints within the Deep Learning process directly from and specific to the input data. This makes it possible to automatically derive cohort-specific biomarkers by using specific data cohorts (e.g. different populations in the case of medical imaging) as the system's input, removing the need to manually design and evaluate biomarkers that are optimized for those groups. This is a big step towards precision medicine as the system can use a biomarkers and machine learning models that are optimized for a given patient.

The proposed system supports three modes of operation:
a) Discriminative only: Only discriminative loss, no semantic losses. Output: a classifier, e.g. for machine learning in decision support systems. This is the default mode of operation for established Deep Learning approaches.
b) Semantic Constraints only: No discriminative loss, only semantic losses. Output: Qualified features. A novel way of automatically deducing qualified and calibrated features (RADIOME) from given input images.
c) Semantic and Discriminative: Discriminative loss+ semantic losses. Output: Qualified features (qualified RADIOME) as biomarkers and classifier(s) based on them. This novel technique produces a model that is calibrated and interpretable by way of the integrated semantic constraints and diagnostically relevant.

For the mode "Semantic and Discriminative", the discriminative loss (evaluated at the output layer) and the semantic losses (evaluated at inner nodes) can either be computed alternatively or jointly. The preferred embodiment of the system computes them jointly to ensure that the combined loss decreases in every iteration of the optimization procedure despite the discriminative part depending on the biomarker-enabled features.

In contrast to the traditional discriminative loss, the semantic losses are not necessarily evaluated at the network's final layer, but on its inner nodes, usually lying before the classification layer(s). The system is capable of enforcing these constraints at any number of nodes in the network, rendering the outputs of these nodes biomarker-enabled features. In an exemplary embodiment (see FIG. 2), the semantic constraints are enforced at all nodes with a direct output connection to the classification layers. The output of the system is thus a model that lends itself both to machine learning tasks—it is discriminative due to minimizing the discriminative loss—as well as biomarker research—the features derived by the network underwent a rigorous qualification procedure due to the imposed semantic constraints.

Different semantic constraints require different types of input for computing the corresponding loss. Several dimensions exist in the data. Using medical imaging for illustration, examples are different patients, different time points of the same patient, different measurements in the same image, different variations of the same image and image dimensions. Each constraint needs a subset of these dimensions as its input. The proposed system supports different mappings of these dimensions to components of the neural network. These components include:
1. Multiple input weights to the neuron computing or evaluating the feature.
2. Multiple shared-weight copies of the network part that computes the feature.
3. Multiple input data instances of one (mini)batch used for evaluating the loss.

While the first two points are commonly used, the third point requires explanation. Theoretically, the loss can be computed for each data point (e.g. each image) and back-propagated to tune the network's weight. For reasons including computation speed, state-of-the-art systems often compute and propagate the loss jointly for groups of data points, so-called minibatches, instead. The novelty of the proposed system here is that by carefully selecting the semantics of the data points in one minibatch and using novel loss functions, data in one minibatch can be analyzed for its overall properties instead of per data point.

Example uses of these techniques in the preferred embodiment for medical imaging include:
1. Multiple weights: Image dimensions.
2. Multiple shared-weight copies: Variations of the same input image, e.g. with added noise.
3. Multiple input data instances of one minibatch: Different patients.

An example for a combination of different measurements in the same image and multiple data instances of one minibatch can be found in the SALSA technique. The combination of SALSA with our semantic constraints is thus the second principal idea of our proposed system. Here, different features are used for regions containing the object of interest (e.g. tumor) which we call RADIOME and control regions only exhibiting technical variation (e.g. surrounding air in a CT scan) that are used to construct the TECHNOME. Different, potentially parallel parts of the network compute these two sets of features. In the end, one or more features of interest and one or more technical variation features can be used as the input to the same neuron. That neuron, defining a novel neural network layer type, relates the features in the two regions across data points (e.g. patients) in one minibatch. Its output can then be used as an input to a semantic loss function—in the simplest form the novel neuron can already compute a loss and forward it to a loss function that simply returns it. In medical imaging, the same technique can be used to relate features computed in in vitro images i.e. phantom scans to those of in vivo scans i.e. real patients.

Examples for semantic constraints that can be enforced by the proposed system include:
Decorrelation of features (algebraically, by correlation or information-theoretic measures)
Scanner-specific knowledge, e.g. properties of measurements across reconstruction kernels in medical imaging
Enforcing the similarity of measurements in regions of the same image while ensuring dissimilarity to those in different images
SALSA constraints to identify in vivo image quality surrogates and employ them to standardize the RADIOME within the Deep Learning network (see FIGS. 1, 2, 5):
  Association: Association of features in ROI to features in control regions e.g. air to construct the TECHNOME. The TECHNOME is constructed via associations that should not be there e.g. association of air and tumor.
  Association of features in ROI to features that were identified in phantom scans to show strong response to technical variation by scan parameters to construct the TECHNOME.
  Non-association of features in control regions with clinical annotations (response variable) to construct the TECHNOME.
  Similarity and linearity of association of features in ROI and features in control regions with the associations of these features found in in silico studies to construct the TECHNOME.
  The last constraint is that the RADIOME image filter is developing orthogonally to the TECHNOME image filter (decorrelation of RADIOME and TECHNOME). This decorrelation translates to the effect that TECHNOME features are correcting the RADIOME features for the impact of technical variation while the RADIOME is simultaneously predicting the diagnostic relevant clinical response.
  The corrected RADIOME image filters can be constructed to be orthogonal to a so-called benchmark model that was created using the induced TECHNOME image features and uses them to predict the response variable. This also safe-guards against poor study design, as such a benchmark model that was created only using information from image regions that can't contain most of the biologically relevant information should only be able to predict the response variable if the response is confounded with acquisition or reconstruction parameters.

We further propose an interchangeable output format, enabling individual business-specific qualified biomarker processing, as these biomarker image filters are the output of the proposed system and evidentially perform better than correlated features. Thus, our system can serve as a general, inevitable preprocessing for various domains, e.g. within the scope of drug trials or clinical studies, as well as further Machine Learning or Deep Learning approaches for specific cohorts or clinical institutions. The outputs of our proposed system can even serve as the input to solutions implemented by big market competitors or specialized startups. Concretely our system can produce the following output formats (FIG. 8):

RADIOME filter image array (RFI), consisting of a variety of filtered images—called filter maps—, which were successfully uncorrelated from technical variations through our proposed system. RADIOME filter image arrays use an open encoding and thus can be used as "corrected input images", especially for further Deep Learning or, more generally, Machine Learning. As the preprocessing was performed independently of a clinical question ("target"), they can be used for a wide variety of tasks, including, but not limited to: medical studies, decision support systems or cohort specific clinical trials.

RADIOME feature array (RFA). RFAs follow an open encoding and can be used as a more-preprocessed form of the previously mentioned RADIOME filter maps. They are specifically targeted to fit the requirements of clinical studies, as they are already reduced to the most important features, also enabling a wide variety of tasks.

Specialized RADIOME features (RFS)—RADIOME features contain an already target-specific pre-conditioned version of the RADIOME feature array. They differ from the aforementioned formats in being specialized for a specific task and thus are more promising for finding existing effects for those tasks. They are especially targeted to end users, mostly clinical partners or software suppliers, which lack extensive knowledge on machine learning or advanced statistics. As specialized RADIOME features are specific to concrete customers, they don't necessarily follow an open standard, but can also be encrypted to prevent misuse.

Precisely, we propose two main distributional channels:

Intelligent Scanning—Real-Time Feature-Enhanced Computed Tomography: When using scanners which use the present invention, the corrected RADIOME features are written directly into the reconstructed images. Due to the close link between scanner physics and RADIOME feature correction the scanner itself is the perfect place for feature correction as it provides a huge amount of additional parameters conducive for feature correction. Corrected features can thus be compiled directly into the DICOM files and sent to the PACS. This compilation takes place either a) as additional DICOM frames (RADIOME filter image arrays), or b) as DICOM metadata (RADIOME feature arrays), depending on the concrete type of data included. Hence, the resulting feature augmented images can subsequently be used for faster, more reliable disease assessment using qualified image features, generating a considerable competitive advantage for Scanners which use the present invention.

FaaS—Feature-Correction as a Service: For cases where patients either a) were not scanned with scanners which use the present invention, or where b) algorithms should be applied on DICOMs without corrected feature meta information, we propose two different ways of utilizing our feature correction as a service for external data:

Online-Service-variant: Patient image data can be uploaded to a cloud-based web service for a fee. The web service applies the SCDL-system to the data, thus corrects correlations to biologically irrelevant regions, augments the DICOM image and subsequently sends back the data to the institution. This scenario is especially interesting for clinical or academic institutions, willing to use the data as a basis for scientific research Model-Zoo-variant: As our system can be capsulated into a black-box-like preprocessing, taking DICOM images as input and dispensing corrected features and feature maps as output, the system can be integrated as a preprocessing layer for various deep learning or general machine learning applications, and thus for enhanced computer aided diagnosis and assessment. The system will be provided as an encrypted, license-based, model layer, integrable into common deep learning and machine learning frameworks, and also be integrated into other scanner applications or competitor products. Thus, this scenario is especially interesting for big market competitors.

To the best of our knowledge, the proposed system comprises the only solution generating generally usable, qualified biomarkers that are uncorrelated to technical variations. Prospectively, additional constraints can be specified by the customer e.g. the RADIOME being decorrelated from epidemiologic covariates. Thus, using our solution is a) highly discernable, b) suitable for large market segments, and c) an outright unique selling point.

After the proposed system creates the standardized diagnostically relevant biomarkers, it compares their associations with already established and interpretable hand-crafted features, for example by computing the linear or nonlinear correlation to them. By relating the newly derived standardized features to existing ones that are already accepted by radiologists or custom in the daily clinical practice, the user's understanding of and confidence in the system can be increased even more.

To further enhance the interpretability we propose a "Biomarker Octagon" to visualize the standardized diagnostic relevant features but also information regarding the image quality for each patient, especially the image quality parameters with highest relevance for the diagnostic task (see FIG. 6). While the system also allows enforcing the similarity to well-known features as a semantic constraint during training, this is not enabled in the preferred embodiment to allow the system to discover novel, previously unknown features.

As special application the proposed system allows to construct "Discriminative only TECHNOME" models that can be used as a benchmark for the validity of a study design i.e. it is analyzed whether the Deep Learning classification or regression is already sufficiently covered via analysis in control regions such as air.

To the best of our knowledge, the described system is the only one that allows

Integrating semantic constraints such as SALSA in the Deep Learning system, thus automatically deriving standardized image features from a region of interest and control regions as well as an optimal classification or regression simultaneously and automatically from the input data. The TECHNOME and the RADIOME in SALSA [cp. EP 17 196 657] are constructed simultaneously by way of Deep Learning. The mathematical model to construct a TECHNOME is now transferred to the Deep Learning setting. The TECHNOME-guided image filters as proposed in SALSA are transferred to the Deep Learning setting, finding an efficient and novel solution.

Concluding from the argumentation of the first point we furthermore propose Deep Learning benchmark systems that use Deep Learning in control regions such as air for diagnosis. If the classification is successful the diagnosis is guided by non-biological image content indicating a deficient study design that needs to be corrected via TECHNOME-based semantically constrained deep learning.

Integrating epidemiologic data in all layers of the Deep Learning network (epidemiologic covariates) that enables the features derived by the network to capture additional diagnostically relevant information orthogonal to those covariates. The Deep Learning image filters focus on the information that explicitly needs a CT scan and is not already covered by other sources (e.g. BMI, blood parameters). This is expected to enhance the performance of the Deep Learning system in general while requiring fewer data than existing systems due to a decrease of non-explained variability (cp. statistical power), embedding further a-priori information about the imaging-system-specific acquisition and reconstruction process into a Deep Learning procedure, creating a competitive advantage for scanners which use the present invention.

Visualizing Deep Learning filters and filter outputs where the impact of undesired technical and epidemiological associations is suppressed by semantic constraints thus enabling to concentrate on a visualization of the biological association with the response variable e.g. tumor malignancy without the impact of spurious correlations.

Automatically deriving cohort-specific biomarkers when using a specific cohort as input.

Reducing the search space of the Deep Learning optimization to semantically meaningful values, making it more likely and faster to converge to a useful result.

Novel use of across-minibatch loss functions to interrelate measurements of multiple images/patients in a meaningful way.

Simultaneously integrating the biomarker qualification process and the calibration within the Deep Learning classification process.

To enhance interpretability of results we propose a "Biomarker Octagon" that correlates the qualified image filters/features with semantic radiological criteria and image quality parameters to translate the results of the Deep Learning system to interpretable measures.

Our system uses novel interchangeable output formats RFI, RFA and RFS. RFI stores the standardized i.e. decorrelated output images, RFA standardized feature arrays and RFC standardized biomarkers for specialized tasks.

FIG. 1 schematically shows the extraction of a feature of interest, especially a biomarker, from an input image 1 and an approach for decorrelating this feature of interest from the impact of a technical imaging parameter, e.g. a noise level in the input image 1. The approach discussed with respect to FIG. 1 can be implemented by a machine learning network. The feature of interest can be extracted from an inner node of this machine learning network by applying semantic constraints to at least one inner node of this network. This will be discussed in more detail later on.

The input image 1 depicts at least a section of an object 2 of interest, namely a heart of a patient. The input image 1 can be presegmented. Image data of a region of interest 3 depicting the object 2 can be processed by a machine learning network to generate a feature 5 of interest. The feature 5 can be a biomarker that is connected via a biological association 7 to a biological state or condition of the patient. The machine learning network can provide a probable biological state or condition or a probability for a certain biological state or condition as the output 6 of an output layer of the machine learning network. This can e.g. be achieved by using supervised training, e.g. by providing a training dataset that comprises several input images 1 and a desired output 6 for each of the input images 1. The machine learning network can e.g. be an artificial neural network trained by back prorogation of error.

Once a machine learning network is trained to generate the desired output 6 for the training dataset and therefore also for input images 1 that are similar to images of the training dataset the output of any node of the machine learning network that is used as an input for the output layer can in principle be considered to be a feature 5 of interest, since all the features are used by the machine learning network to determine the output 6. When a machine learning network is trained by this conventional approach, it works as a black box, wherein the outputs of individual inner nodes of the machine learning network are typically sub-symbolic and can therefore not easily be associated with specific biological or technical features. It is therefore e.g. not known, if the output of a node that feeds the output layer of the machine learning network is mainly determined by a feature of the object 2 of interest, by imaging parameters or by other parameters of a patient, e.g. by his or her body mass index or weight. Typically, outputs of inner nodes depend on all the mentioned factors.

This is problematic for several reasons. If e.g. the actual input image 1 uses different imaging parameters than the input images 1 used during the training of the machine learning network this might lead to unexpected changes of the output 6 of the machine learning network. The machine learning network is therefore not necessarily robust with respect to changes of imaging parameters or other parameters of a patient. It is also disadvantageous that the medical professional using the provided data can not interpret the features 5 since they are dependent on a variety of very different factors. The only usable output is therefore the final output 6 of the machine learning network. Since this output is generated by a machine learning network acting as a black box the output 6 needs to be validated by other methods. The usefulness of the output 6 in determining a diagnosis might therefore be limited.

As discussed in more detail later on the outputs of inner nodes can be embedded with meaning and especially act as biomarkers if additional constraints are applied to the outputs of the inner nodes of the machine learning network during the training. FIG. 1 shows a principle approach for decoupling features 5, 11 of interest that concern the region 3 of interest and especially the object 2 of interest and features 8, 12 concerning a control region 4 outside of the object 2 that concern technical features of the imaging process and/or further parameters of the patient not concerning the object 2.

To remove a dependency of the features 5 on influences caused by technical parameters or certain parameters of a patient algorithms should be chosen that determine features 8,12 of the TECHNOME from the image data of the control region 4 that have a semantic additive linear surrogate association 9 with the features 5, 11. Surrogates provide a measure for certain technical parameters or patient parameters that should be decorrelated from the parameters 5, 11. The association 9 is additive and linear if the right algorithms are chosen. In this case a decorrelation 10 or suppression of this association can simply be achieved by subtracting scaled parameters of the TECHNOME from the parameters of the RADIOME. Algorithms for extracting a TECHNOME can be determined by providing a large number of algorithms and using certain conditions for selecting the chosen algorithms. This approach is discussed in the presently not published European patent application EP 17 196 657, the entire contents of which are hereby incorporated herein by reference. As discussed in more detail below it is however possible to train a subnet of the machine learning network used to extract the features 5, 8, 11, 12 in such a way that the subnet extracts a TECHNOME, especially as the output of one or more inner nodes of the machine learning network, in a way that satisfies the desired association 9.

The discussed steps of extracting a TECHNOME 8, 12 that has a semantic additive linear surrogate association 9 with the extracted RADIOME can be iterated. In the case of machine learning this iteration automatically happens during the learning procedure. The machine learning network could e.g. be first trained to provide a desired output 6, afterwards constraints for the outputs of inner nodes could be applied to generate the desired features 8 of the TECHNOME and features 5 of the RADIOME and a decorrelation 10 can be applied. Afterwards, the pre-trained network can be trained further to provide a corrected desired output 13 and constraints could be applied afterwards to train the network to provide corrected features 11 of the RADIOME and corrected features 12 of the TECHNOME. This process can be repeated for a given number of times or until certain conversion criteria are fulfilled.

In the previously discussed approach the training is alternated between using the constraint for the output 6, 13 of the output layer of the machine learning network and using constraints for the outputs of inner nodes of the network. In a preferred embodiment these constraints are applied at the same time and the training is performed while a constraint applies to the output 6, 13 of the output layer of the network and to the output of several inner nodes.

Figure 2:
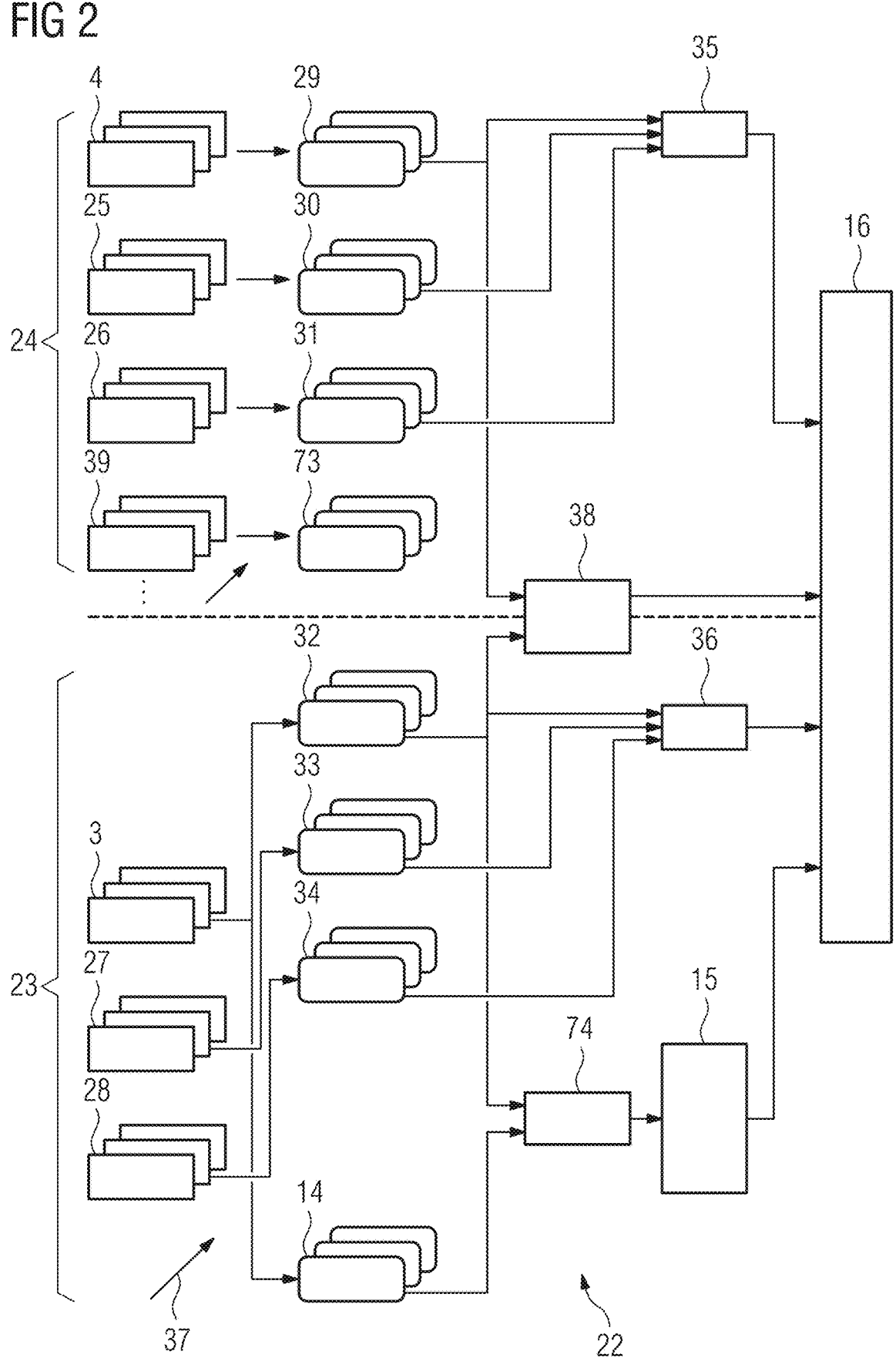

FIG. 2 shows an example of a machine learning network 22 that can be trained to extract features of interest from an input image 1, wherein constraints for inner nodes of the machine learning network 22 are used to force the features of the RADIOME determined for the region of interest to be essentially independent of technical parameters of the image acquisition and/or patient parameters. In FIG. 2 the training mainly concerns the decoupling of the RADIOME features from a noise level in the input image 1. During the training a merged network is used that uses several identical copies of certain sections of the machine learning network 22 to process a minibatch or subset of the training dataset at once. This can be used to monitor and constraint the behavior of the outputs of the inner nodes with changing input images.

In a conventional machine learning network that is trained to classify an object of interest 2 in a region of interest 3 or to perform a regression analysis on a certain parameter of the object 2 of interest only input data from the region 3 of interest would be used. The input data would be fed to an input layer of a subnet 14 that performs an image filtering. Multiple subnets 14 could be used or the subnets 14 could output several output parameters. In a conventional network the outputs would be directly sent to a classification or regression subnet that provides the output of the network 22 at an output layer 15 of the network 22. To train this network 22 input images 1 of the training dataset could be provided with an additional information that describes a desired output of the output layer of the network 22. The difference between the actual output and the desired output is fed to a loss-function 16 that is minimized, e.g. by backpropagation of error in an artificial neural network.

The previously discussed data from at least one control region 4 can be used to determine the effect of imaging parameters or other parameters that are expected to be independent of the object of interest 2. Therefore, the machine learning network 22 uses two sets of input data, the input data 23 taken from the region 3 of interest and the input data 24 taken from at least one control region 4. In the example we want to decouple the RADIOME from the image noise. We therefore generate two modified images for each input image 1 wherein the noise is increased with each modification step. We therefore use the region 3 of interest, a copy 27 of this region with an increased noise level and another copy 28 of this region with a further increased noise level as the input data 23 and the control region 4 and copies 25, 26 of the control region 4 with increasing noise levels as input 24.

Figure 3:
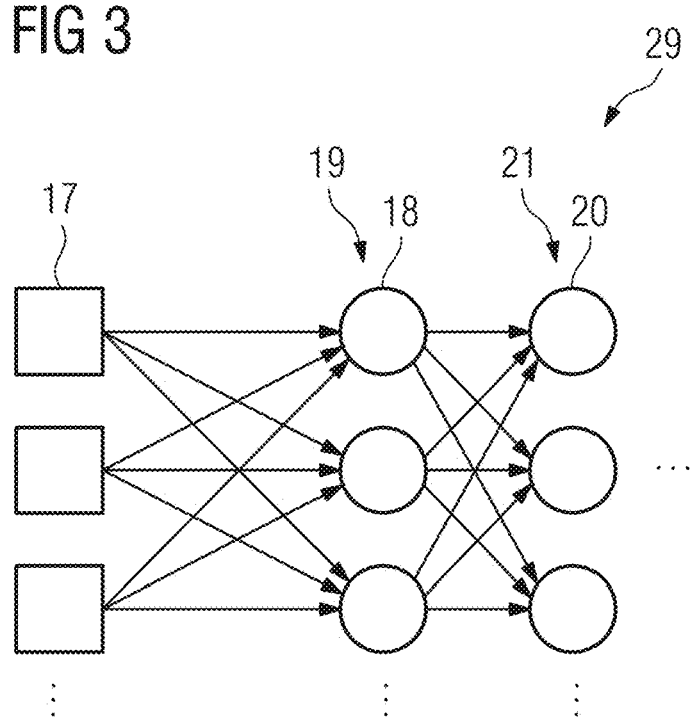

The network 22 comprises a subnet 29 that will be trained to output a feature on its output node that describes a noise level in the respective image. The structure of this subnet is in principle identical to the structure of the subnet 14 and is shown in FIG. 3. Multiple items of input data 17 are fed to multiple nodes 18, e.g. artificial neurons, of an input layer 19. The individual neurons can e.g. calculate a weighted sum of the inputs e.g. implement a convolution filter. It can be advantageous to shape the output of the individual neurons 18 by a respective activation function, e.g. to simulate the switching behavior of actual neurons. It is possible to feed all input data to each node 18 or to feed only some of the input data to each node 18, e.g. a small square or cube of the input data can be fed to each node 18.

While it is in principle possible to implement the complete image filtering within the input layer, it can often be advantageous to implement at least one hidden layer 21 to implement further processing by the nodes 20 of this layer. The nodes 20 can already provide the output of the subnet 29 or further layers can be added.

The parametrization of the subnets 14, 29, especially the input weights of the individual neurons 18, 20 is only determined in the learning process. It is e.g. possible to initially use random input weights, identical input weights for all nodes or any other distribution. To teach a determination of a noise level to the subnet 29 a constraint is applied to the output node of the subnet 29. To implement this constraint two identical copies 30, 31 of the subnet 29 are used. These copies 30, 31 use the copies 25, 26 of the input data of the control region with increased noise levels as input data. Therefore, a subset of images fed to the network 22 and the relationship between the outputs of the subnet 29 and the copies 30, 31 are analyzed. This can be performed by a processing node or a layer 35 that provides inputs for the outputs of the inner nodes of the subnet 29 and the copies 30, 31 to which the constraint is to be applied. The layer 35 can e.g. perform a regression for the outputs of the subnet 29 and the copies 30, 31 and output a regression error. The output is added as an additional factor to the loss-function 16 which leads to a training of the subnet 29 towards recognizing noise.

For the purpose of training the network 22 it is highly relevant that the output of the nodes of the subnet 29 also reproduces the noise level when it is applied to the region of interest. Therefore, further identical copies 31, 33, 34 of the subnet 29 are used that process image data from the region 3 of interest and from copies 27, 28 of the region 3 with added noise. A further processing layer 36 analyses the outputs of the nodes of these copies 32, 33, 34 and determines a loss due to a lack of linearity that is also fed to the loss function 16.

Another important feature of the algorithm implemented by the subnet 29 should be that it behaves in a similar manner when applied in the region of interest and when applied in the control region for a large cohort of patients. This condition can be enforced by a further constraint on the output of the subnet 29 and its copy 32. As indicated by the arrows 37 and the stacking of the input data 23, 24 and the subnets 14, 29 and the copies 30-34 a multitude of images and therefore a minibatch of the input images of the training dataset can be processed in parallel and the similarity of the behavior of the outputs of the subnets 29, 32 can be analyzed. This can be performed by an additional processing layer 38 that can e.g. calculate a measure of the similarity or dissimilarity, e.g. by calculating the correlation between the output of the subnet 29 and its copy 32 across a multitude of input images. A measure of the dissimilarity of these outputs is fed to the loss-function 16.

With the mentioned constraints, the subnet 29 is trained in such a way that the output of the nodes of its final layer that are inner nodes of the machine learning network 22 is a measure of the noise of a respective input image for the control region as well as for the region of interest. To further improve the training it would e.g. be possible to evaluate data from a second control region 39 by another copy 73 of the subnet 29 and e.g. use constraints that enforce a similar behavior of the algorithm implemented by the subnet 29 across multiple control regions 4, 39.

There are two possible ways in which the training of the subnet 29 to detect noise levels can be used to reduce the dependence of the output of the subnet 14 and therefore the dependence of the features of the RADIOME on the noise level and therefore from a feature of a TECHNOME. The first approach uses another node or a layer 74 to calculate a corrected output for the output of the subnet 14 depending on the output of the subnet 14 and either the output of the copy 32 of the subnet 29 and therefore the image data of the region of interest or the output of the subnet 29 and therefore the image data of the control region 4. Since this correction improves the classification or regression result in the output layer 15 the node or layer 74 is automatically trained with the rest of the machine learning network.

Since the output of the inner node or layer 74 is essentially independent of the noise level in the input image it can be considered to be an improved biomarker for the object of interest. The quality of the biomarker could further be improved by applying additional constraints to inner nodes of the machine learning network 22 which e.g. enforce an independence from further imaging parameters, a body mass index of the patient etc.

Alternatively, the subnet 14 could be directly trained to be decorrelated from the output of the copy 32 of the subnet 29 and therefore from an expected noise level in the image. This could e.g. be enforced by calculating a measure of correlation for these outputs and feeding it to the loss function 16.

Figure 4:
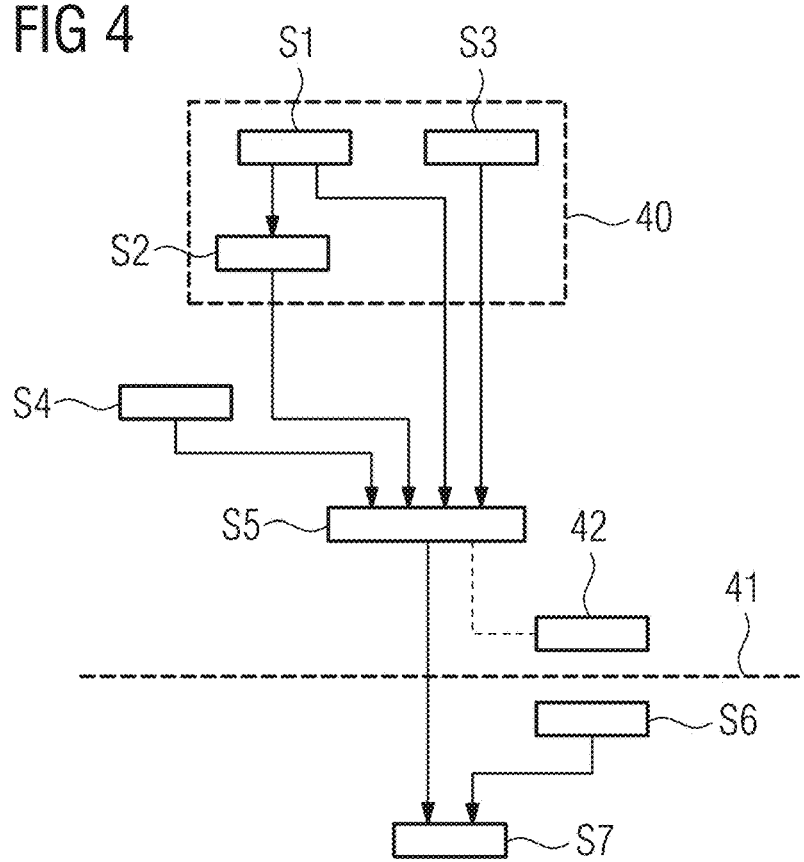

FIG. 4 shows a flow chart for training a machine learning network and using it to extract features of interest, especially biomarkers, from an input image. In step S1 a multitude of input images is recorded. The input images can be recorded with a multitude of medical imaging devices of a certain type, e.g. a multitude of computer tomographs. It is also possible to only use a specific type of device for recording images when the network should be specifically trained to process images from that device. Images can be acquired from patients, especially patients from a certain cohort, e.g. a certain age group, towards which the machine learning network would be trained. At least some of the images can then be modified in step S2. Like discussed with respect to FIG. 2 increased levels of noise can be added to at least some of the images. It is also possible to add blurring and other modifications simulating changes in the imaging parameters. It is also possible to generate some input images of a training dataset 40 in step S3 by simulating the imaging procedure.

In step S4 a basic untrained machine learning network is provided and trained in step S5 using the training dataset 40 generated in the steps S1 to S3 and constraints as explained with respect to FIG. 2. At this point a method for training a machine learning network is complete as indicated by the line 41. The trained machine learning network can then be used to process an input image that is recorded in step S6 in step S7. It s possible to directly provide the processing within a medical imaging device used in step S6 to record the image. It is however also possible to perform step S7 on a processing system that is a separate device from the medical imaging device used in step S6, e.g. step S7 can be performed by an internet server, especially as a service provided to a large group of end users, e.g. hospitals.

Besides the trained machine learning network step S5 can also generate large amounts of features of interest, especially of biomarkers, from the input images of the training dataset 40. This can e.g. be the output of the node or layer 74 in FIG. 2. This output dataset or a subset of this dataset can be useful to train other machine learning networks used in medical imaging, since the provided features and/or biomarkers are approximately independent of the recording conditions and therefore provide a more accurate overview of the distribution of certain features in biomarkers in a patient population than data that is not corrected for the influence of technical features. The dataset 42 can also be used to generate subsections of the dataset, e.g. average values for relevant biomarkers, that can be used in clinical studies or provide reference values for diagnostic purposes.

Figure 5:
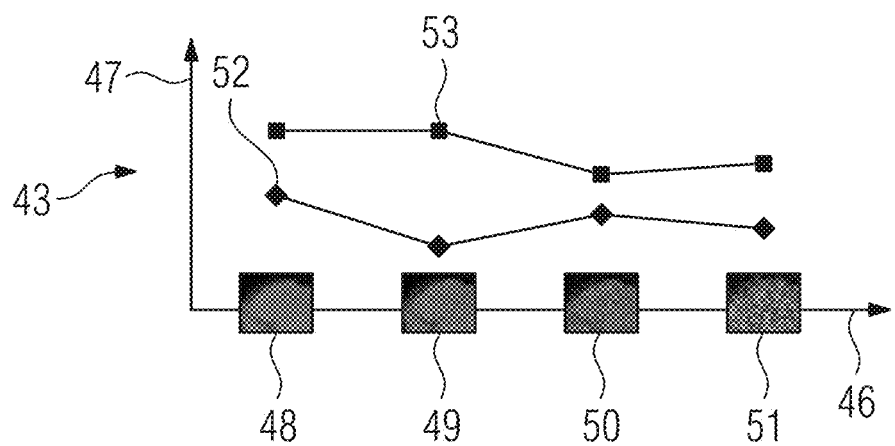
Figure 5:
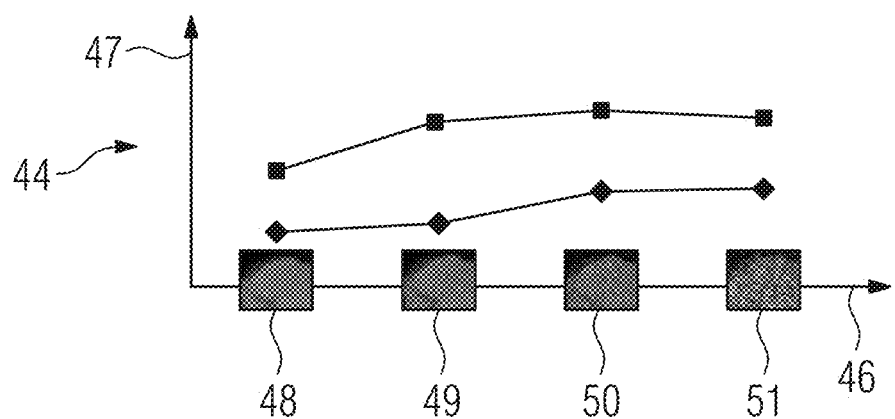
Figure 5:
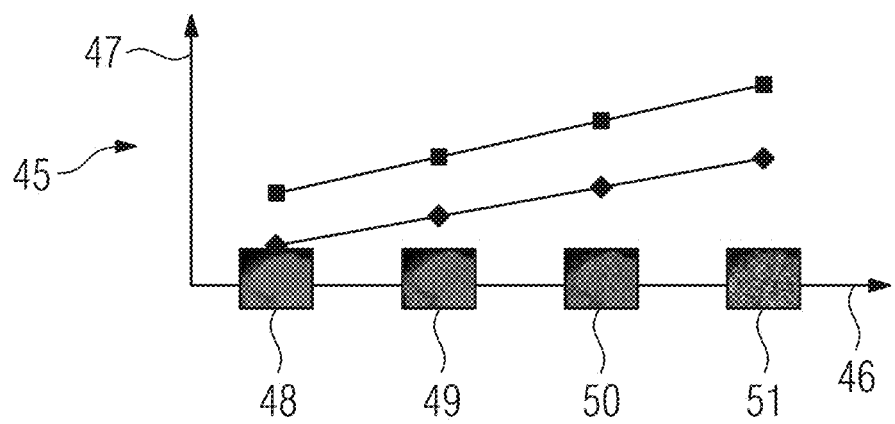

FIG. 5 shows three plots 43, 44, 45 that show the relation between the value of a TECHNOME feature shown on the x-axis 46, e.g. the output of the subnet 29 which will be equivalent to a noise level after training the network, and the value of a RADIOME feature on the y-axis 47, e.g. the output of the copy 32 of the subnet 29 in FIG. 2. Examples of four input images 48-51 with four different noise levels are shown. The plots 43, 44, 45 show the RADIOME feature value for a certain TECHNOME feature value for simulated noise levels as the diamonds 52 and for noise levels in real data as the squares 53. As shown in the plot 43 after a first training iteration the subnet 29 is obviously not sufficiently trained since the RADIOME feature value is obviously not linear with the noise level and there is a strongly different behavior between the simulated images and the real data. With another training iteration the association between a RADIOME feature value and a TECHNOME feature value starts to approach a linear relation and there is also a certain similarity of behavior between the simulated images and the real data as shown in plot 44.

After the training of the machine learning network 22 is complete and therefore after the last iteration of the training process the constraints are successfully enforced and the dependence of the RADIOME feature value on the TECHNOME feature value and on the noise level is linear and behaves similar for synthetically created images and real image data as shown in plot 45.

By using constraints on inner nodes of the machine learning network a certain meaning of certain inner nodes can be enforced. Therefore, the constraints can be considered to be semantic constraints. This can be used to provide a multitude of features that are relevant for a medical professional, especially for forming a diagnosis of a patient.

FIG. 6 shows a possible way to visualize a multitude of such features of interest, at least some of which can be biomarkers.

A polygon 54, especially an octagon, can be used, wherein each corner 55 is assigned to a feature of interest to be visualized. The length of a respective bar 56-63 can show the value of the feature of interest with respect to a reference value that is exactly at the respective corner 55 of the polygon 54. Different types of features of interest can e.g. be visualized by choosing appropriate colors or textures for the bars 56-63. E.g. a first color can be used for the bars 56-58 that show values for well-known biomarkers, e.g. a spicularity and a heterogeneity in the region of interest. The outputs of the respective nodes that provide these values can be forced to behave like the well-known biomarkers e.g. by providing values for these biomarkers with each input image in the training dataset and training the outputs to behave similar to the value of the biomarker provided with the respective input image.

Further bars, e.g. the bars 59-61, can be used to visualize biomarkers that were discovered by machine learning. These biomarkers can already be decoupled from an influence of technical features and also from parameters of the patient or the object of interest that are known from other sources. The user therefore is provided with a multitude of known and new biomarkers and can easily compare them with typical values of the respective biomarkers, especially in a certain patient cohort. This helps the user to form a diagnosis.

Some of the features, e.g. the features displayed by the bars 62, 63, can also be features of the TECHNOME, e.g. a noise level or some other measure of the image quality. Users can therefore see at a glance if the values of the displayed biomarkers are based on a high-quality image and therefore probably have a high accuracy or if the image quality was low which might influence the quality of the resulting biomarkers.

FIG. 6 therefore shows an interpretable biomarker octagon with standardized RADIOME expression and class information. Different line types or bar types indicate different major classes of the examined diagnostic question, e.g. tumor growth extracted from expert ratings. The corners of the octagon represent the average of the criterion over a whole set of reference image data.

FIG. 7 shows a medical imaging device 66 that comprises a processing system 67 that is configured to perform the previously discussed method for extracting features of interest from an input image. The processing system 67 can e.g. comprise a memory unit 68 for storing a computer program comprising instructions for performing the previously discussed method. The instructions can be executed by a processor 69 to perform the method.

While the use of the processing system 67 that is integrated into a medical imaging device 66, e.g. a computer-tomograph, can be advantageous, since such a processing system 67 can have access to parameters that are typically not stored with image data, it can also be useful to provide processing systems 70, 72 that are implemented as separate devices. This can be useful when a medical imaging device is used that can not implement the discussed method. Image data can e.g. be processed by a processing system 70 that is located in the same building 71 as the medical imaging device 66. It can e.g. be a computer located in a control room used to visualize image data acquired by the medical imaging device 66 for a user. Alternatively, an external server can be used as the processing system 72. The processing system 72 can e.g. be an external server or a cloud-based service that e.g. allows a user to upload an input image, e.g. part of the DICOM-file, wherein the server or cloud service will send back at least one feature extracted from the image data.

FIG. 8 shows a visualization of the Deep Learning output of the corresponding Deep Learning network layers. A RADIOME filter image array 64 can comprise the outputs of all or most nodes of a machine learning network. A RADIOME feature array or a selection of specialized RADIOME features 65 can provide a selection of these outputs.

Some further features of the invention will now be discussed with respect to FIGS. 1, 2 and 5.

FIG. 1 shows the construction of a TECHNOME (in a control region CR) and a RADIOME (in a region of interest ROI). After an initial guess of the RADIOME to predict the probability of a major cardiac event, the TECHNOME is constructed to standardize the RADIOME. After the decorrelation of RADIOME and TECHNOME, the RADIOME again tries to predict the probability of a major cardiac event. All these interactions can be modelled simultaneously by semantic constraints.

FIG. 5 shows a semantically constrained deep learning process inducing one qualified TECHNOME feature being measured in a control region (CR). The associations between RADIOME and TECHNOME are shown for different images of real data (plot: square) or synthetic data introduced by simulations (in this case additive Gaussian noise) (plot: diamond). The images along the x-axis illustrate the four levels of noise using a CT image of the ROI heart and the surrounding tissue. The three plots show the progression of the TECHNOME-RADIOME association towards being both linear (feature values behave linearly with increasing image noise) and similar in real and in synthetic (in this case added noise) image data.

FIG. 2 shows an example of a Deep Learning architecture with integrated semantic constraints.

We want to give a brief introduction of how to combine our proposed system with SALSA i.e. feature standardization in a ROI via control regions (FIG. 1). The image filter within a ROI evolves according to the biological problem to predict—in the shown example the probability for a major cardiac event. Next the image filter within the CRs i.e. the TECHNOME evolves in a manner that it maximizes the association with the image filter within the ROI i.e. the RADIOME in a way that can be reproduced in a similar fashion in advanced simulations also preferring least complex associations which are linear. If this first TECHNOME can already explain the RADIOME in a manner that is similar to simulations of technical variation, the RADIOME information within the ROI is not specific to the ROI but also contained in non-relevant image regions such as CRs, and is also induced technically. To suppress this association the TECHNOME is decorrelated from the RADIOME iteratively by semantic constraints i.e. by semantic network losses which iteratively improve the network by backpropagation. In the next iteration the RADIOME is again conditioned to predict the major cardiac event and the new TECHNOME evolves according to the semantic constraints.

In FIG. 5 we show two exemplary semantic constraints. The image filter within the CRs (TECHNOME) evolves such that its association with the current image filter within the ROI (RADIOME) is linear and similar to the associations of RADIOME and TECHNOME in simulated data. The plot marked by squares 53 visualizes the association between RADIOME feature value and TECHNOME feature value for 4 different patients. The plot marked by diamonds 52 shows the association between RADIOME feature value and TECHNOME feature value for 1 patient with increasing simulated noise levels. Via semantic constraints the TECH- NOME image filter evolves in a manner that its association with the RADIOME feature value is linear and similar to the simulated data. The two presented constraints are examples of how to construct a suitable TECHNOME.

In FIG. 2 we show an example for a Network Architecture and for how semantic constraints can be combined with the usual "discriminative" loss to form a combined Deep Learning architecture in the proposed system. Here, the semantic constraint of linearity across noise levels is enforced separately in ROI and control regions to identify image features that capture noise. Additionally, those features must behave similarly for RADIOME and TECHNOME to verify them, which is captured by a second type of semantic constraint. Using another semantic constraint, the features that were generated like this to capture noise are then forced to be decorrelated from a second set of features that was created for the ROI and captures biological variation, which is enforced by the discriminative loss (layer 15). Not depicted here: a) Semantic constraints that can be enforced across different control regions CR1, CR2 etc., e.g. to enforce similar behavior across noise levels. b) Semantic constraints that can be enforced across patients.

Although the present invention has been described in detail with reference to the preferred embodiment, the present invention is not limited by the disclosed examples from which the skilled person is able to derive other variations without departing from the scope of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for obtaining at least one feature of interest from an input image acquired by a medical imaging device, the at least one feature of interest being an output of a node of a machine learning network, the method comprising:

processing, via the machine learning network, at least part of the input image acquired by the medical imaging device as input data, the machine learning network being configured to process image data of a region of interest of the input image and at least one control region of the input image, and at least one of the at least one feature of interest and an output of an output layer of the machine learning network depending on the image data of the region of interest and the at least one control region;

training the machine learning network by machine learning using at least one constraint; and obtaining the at least one feature of interest from an output of at least one inner node of the machine learning network during the machine learning, wherein at least one of the at least one feature of interest and the output layer of the machine learning network describes a property of an object of interest that is expected to be independent of the image data in the control region, wherein a training dataset used for training the machine learning network comprises additional information for each input image of the training dataset, wherein fulfilment of at least one of the constraints for the inner node or at least one of the inner nodes concerns a dependence or independence between the output of the respective inner node and the additional information for the input images or a subset of the input images in the training dataset.

2. The method of claim 1, wherein at least one of the at least one the feature of interest and the output of an output layer of the machine learning network includes information usable to enable or support a user in forming a diagnosis concerning a patient depicted in the input image.

3. The method of claim 1, wherein the machine learning network is trained using at least one additional constraint for the output of at least one output node of an output layer of the machine learning network.

4. A non-transitory computer-readable storage medium storing electronically readable instructions, for performing the method of claim 1 when the electronically readable instructions are executed on by a processing unit of a medical imaging device.

5. The method of claim 1, wherein the at least one feature of interest is a biomarker.

6. A method for obtaining at least one feature of interest from an input image acquired by a medical imaging device, the at least one feature of interest being an output of a node of a machine learning network, the method comprising:

processing, via the machine learning network, at least part of the input image acquired by the medical imaging device as input data, the machine learning network being configured to process image data of a region of interest of the input image and at least one control region of the input image, and at least one of the at least one feature of interest and an output of an output layer of the machine learning network depending on the image data of the region of interest and the at least one control region;

training the machine learning network by machine learning using at least one constraint; and obtaining the at least one feature of interest from an output of at least one inner node of the machine learning network during the machine learning, wherein a training dataset used in the training of the machine learning network is split into multiple subsets, wherein the training of the machine learning network is includes combining multiple identical copies of one of the machine learning network or at least one subsection of the machine learning network into a merged network, wherein each of the multiple identical copies processes input data from one of the input images of a respective subset, coupling multiple identical copies by at least one additional processing node or processing layer of the merged network providing a respective input for at least two copies of the machine learning network or subsection for the output of the respective inner node or of at least one respective inner node to which the at least one constraint should be applied, and outputting a measure of fulfilment of the at least one constraint depending on outputs of the respective inner nodes of the multiple identical copies.

7. The method of claim 6, wherein at least one of the subsets comprises input images generated by a simulation of the image generation or by a modification of a provided input image wherein a parameter of the simulation of the image generation or the modification is varied across the subset, and wherein the at least one constraint or at least one of the constraints concerns a dependence or independence between the output of at least one inner node of the machine learning network and the parameter varied.

8. The method of claim 6, wherein the at least one feature of interest is a biomarker.

9. The method of claim 6, wherein at least one of the at least one the feature of interest and an output of an output layer of the machine learning network includes information usable to enable or support a user in forming a diagnosis concerning a patient depicted in the input image.

10. The method of claim 9, wherein the machine learning network is configured to process image data of a region of interest and at least one control region of the input image, wherein at least one of the at least one feature of interest and the output of the output layer of the machine learning network describes a property of an object of interest that is expected to be independent of the image data in the control region, and wherein at least one of the at least one feature of interest and the output of the output layer depends on the image data of the region of interest and the control region.

11. A non-transitory computer-readable storage medium storing electronically readable instructions, for performing the method of claim 6 when the electronically readable instructions are executed on by a processing unit of a medical imaging device.

12. A method for obtaining at least one feature of interest from an input image acquired by a medical imaging device, the at least one feature of interest being an output of a node of a machine learning network, the method comprising:

processing, via the machine learning network, at least part of the input image acquired by the medical imaging device as input data, the machine learning network being configured to process image data of a region of interest of the input image and at least one control region of the input image, and at least one of the at least one feature of interest and an output of an output layer of the machine learning network depending on the image data of the region of interest and the at least one control region;

training the machine learning network by machine learning using at least one constraint; and obtaining the at least one feature of interest from an output of at least one inner node of the machine learning network during the machine learning, wherein at least one of the at least one constraint concerns a dependence or independence of at least one first inner node of the machine learning network on or of an output of at least one second inner node of the machine learning network for the input images or the input image, or a subset of the input images in a training dataset used for training the machine learning network.

13. The method of claim 12, wherein the at least one first inner node depends exclusively on data taken from a respective first region of the input image and an at least one second inner node depends exclusively on data taken from a respective second region of the respective input image.

14. The method of claim 12, wherein the machine learning network is designed such that the at least one first inner node generates a same output when the at least one first inner node and the at least one second inner node or a first subnet of the machine learning network comprising the at least one first inner node and a second subnet of the machine learning network comprising the at least one second inner node are processing same input data.

15. The method of claim 13, wherein the at least one first inner node and the at least one second inner node depend on same data taken from the respective input image.

16. A non-transitory computer-readable storage medium storing electronically readable instructions, for performing the method of claim 12 when the electronically readable instructions are executed on by a processing unit of a medical imaging device.

17. The method of claim 12, wherein the at least one feature of interest is a biomarker.

18. A method for obtaining at least one feature of interest from an input image acquired by the medical imaging device, the at least one feature of interest being an output of a node of a machine learning network, the method comprising:

processing, via the machine learning network, at least part of the input image acquired by the medical imaging device as input data, the machine learning network being configured to process image data of a region of interest of the input image and at least one control region of the input image, and at least one of the at least one feature of interest and an output of an output layer of the machine learning network depending on the image data of the region of interest and the at least one control region;

training the machine learning network by machine learning using at least one constraint; and obtaining the at least one feature of interest from an output of at least one inner node of the machine learning network during the machine learning, wherein at least one of the at least one feature of interest and the output layer of the machine learning network describes a property of an object of interest that is expected to be independent of the image data in the control region, wherein a training dataset or at least one of the training datasets used for training the machine learning network comprises input images that where generated by imaging a phantom or by simulation of an imaging of a digital phantom, wherein a technical imaging parameter used in generation or reconstruction of the input image is varied between the input images, wherein the technical imaging parameter or a measure that is dependent on the technical imaging parameter is provided as additional information for the respective input image, wherein the at least one constraint for an inner node, whose output depends on image data from the region of interest of the input image and concerns a dependence between the output of the inner node and the technical imaging parameter or the measure that is dependent on the technical imaging parameter.

19. A processing system, comprising:
at least one processor, configured to obtain at least one feature of interest from an input image acquired by a medical imaging device, the at least one processor being configured to:
  process, via a machine learning network, at least part of the input image, acquired by the medical imaging device, as input data, the at least one processor being configured to process image data of a region of interest of the input image and at least one control region of the input image, and at least one of the at least one feature of interest and an output of an output layer of the machine learning network depending on the image data of the region of interest and the at least one control region;
  train the machine learning network by machine learning using at least one constraint for an output of at least one inner node of the machine learning network during the machine learning; and
  obtain the at least one feature of interest from an output of a node of a machine learning network, wherein at least one of the at least one feature of interest and the output layer of the machine learning network describes a property of an object of interest that is expected to be independent of the image data in the control region, wherein a training dataset used for training the machine learning network comprises additional information for each input image of the training dataset, wherein fulfilment of at least one of the constraints for the inner node or at least one of the inner nodes concerns a dependence of independence between the output of the respective inner node and the additional information for the input images or a subset of the input images in the training dataset.

20. A medical imaging device, comprising:
at least one imaging source;
at least one detector; and
the processing system of claim 19.

21. A computer tomography device, comprising:
at least one x-ray source;
at least one detector; and
the processing system of claim 19, wherein the computer tomography device is the medical imaging device.

22. The processing system of claim 19, wherein at least one of the at least one constraint concerns a dependence or independence of at least one first inner node of the machine learning network on or of an output of at least one second inner node of the machine learning network for the input images or the input image, or a subset of the input images in a training dataset used for training the machine learning network.

* * * * *